United States Patent
Sauer (10) Patent No.: US 11,207,179 B2
(45) Date of Patent: Dec. 28, 2021

(54) VALVE INSERTION TOOL

(71) Applicant: LSI Solutions, Inc., Victor, NY (US)

(72) Inventor: Jude S. Sauer, Pittsford, NY (US)

(73) Assignee: LSI SOLUTIONS, INC., Victor, NY (US)

( * ) Notice: Subject to any disclaimer, the term of this patent is extended or adjusted under 35 U.S.C. 154(b) by 225 days.

(21) Appl. No.: 16/261,319

(22) Filed: Jan. 29, 2019

(65) Prior Publication Data

US 2019/0231524 A1    Aug. 1, 2019

Related U.S. Application Data (60) Provisional application No. 62/622,974, filed on Jan. 29, 2018.

(51) Int. Cl.
| | | |
|---|---|---|
| *A61F 2/24* | (2006.01) | |
| *A61B 17/00* | (2006.01) | |
| *A61B 17/04* | (2006.01) | |
| *A61F 2/00* | (2006.01) | |

(52) U.S. Cl.
CPC ...... *A61F 2/2436* (2013.01); *A61B 17/00234* (2013.01); *A61B 17/0469* (2013.01); *A61F 2/0095* (2013.01); *A61F 2/2427* (2013.01); *A61B 2017/00243* (2013.01); *A61F 2/24* (2013.01); *A61F 2220/0075* (2013.01)

(58) Field of Classification Search
CPC .... A61F 2/0095; A61F 2/2436; A61F 2/2427; A61F 2/24; A61B 2017/00243; H04R 1/1033
See application file for complete search history.

(56) References Cited

U.S. PATENT DOCUMENTS

| | | | | |
|---|---|---|---|---|
| 5,868,253 A | * | 2/1999 | Krueger | A61F 2/0095 206/363 |
| 6,214,043 B1 | * | 4/2001 | Krueger | A61F 2/2427 623/2.11 |
| 2007/0000802 A1 | * | 1/2007 | Keller | A61F 2/0095 206/438 |
| 2009/0259292 A1 | * | 10/2009 | Bonhoeffer | A61F 2/2409 623/1.15 |
| 2011/0214398 A1 | * | 9/2011 | Liburd | A61L 2/0094 53/467 |
| 2012/0158128 A1 | * | 6/2012 | Gautam | B65B 55/18 623/2.11 |
| 2016/0050481 A1 | * | 2/2016 | Moats | H04R 1/1033 381/384 |
| 2016/0295312 A1 | * | 10/2016 | Merenda | A45C 15/00 |
| 2017/0195760 A1 | * | 7/2017 | Tang | B65D 85/671 |
| 2021/0000465 A1 | * | 1/2021 | Kam | A61F 2/0095 |

* cited by examiner

*Primary Examiner* — Ashley L Fishback
(74) *Attorney, Agent, or Firm* — Michael E. Coyne; Christopher B. Miller (57) ABSTRACT

A valve insertion tool is disclosed. The valve insertion tool may be used in a minimally invasive cardiac surgery. The valve insertion tool includes a housing and a cover, the housing having at least one valve recess and a suture channel. The valve insertion tool is suitable for use in delivering a prosthetic heart valve into a thoracic cavity of a patient during a minimally invasive cardiac surgical procedure. One or more valve insertion tools may be stackable and be pre-loaded with one or more prepared prosthetic heart valves. These one or more valve insertion tools may be packaged as a valve insertion kit.

14 Claims, 13 Drawing Sheets

VALVE INSERTION TOOL

RELATED APPLICATIONS

This application claims priority to U.S. Provisional Patent Application No. 62/622,974 filed Jan. 29, 2018 and entitled, "VALVE INSERTION TOOL." The 62/622,974 application is hereby incorporated by reference in its entirety.

FIELD

The claimed invention relates to surgical devices, and more specifically to minimally invasive surgical devices for passing a prosthetic heart valve into the thoracic cavity of a surgical patient.

BACKGROUND

Great advances have been made in cardiac surgery with regard to performing more and more procedures using minimally invasive approaches. For example, aortic and mitral valve replacement are routinely performed using minimally invasive approaches. Most of the surgical actions in such valve replacement surgeries can be done through a very small incision with instruments having shafts often on the order of 10 mm or less. Smaller incisions result in less perioperative pain and better patient outcomes. Unfortunately, a larger incision is often needed to allow the prosthetic heart valve to be inserted into the patient's thoracic cavity. Care must be taken when doing this, as the prosthetic valve leaflets are quite fragile. Therefore, it would be desirable to have an economical and reliable valve insertion tool which would enable insertion of the prosthetic valve into the thoracic cavity through much smaller incisions than are currently available.

SUMMARY

A valve insertion tool is disclosed. The valve insertion tool includes a housing defining at least one valve recess, a suture channel passing from a distal end of the housing to a proximal end of the housing, and a cover configured to engage the housing for covering the at least one valve recess and a top of the suture channel. An alternate embodiment of the valve insertion tool includes a housing where the housing defining a first valve recess and a second valve recess.

A valve insertion kit is also disclosed. The valve insertion kit includes at least one valve insertion tool. The valve insertion tool includes a housing and a suture channel where the housing defines at least one valve recess, and the suture channel passes from a distal end of the housing to a proximal end of the housing. The valve insertion kit also includes at least one prosthetic valve having at least one suture stitched into a sewing cuff on the valve. The valve insertion kit also includes a cover configured to engage the housing for covering the at least one valve recess and a top of the suture channel.

DETAILED DESCRIPTION

Figure 1A:
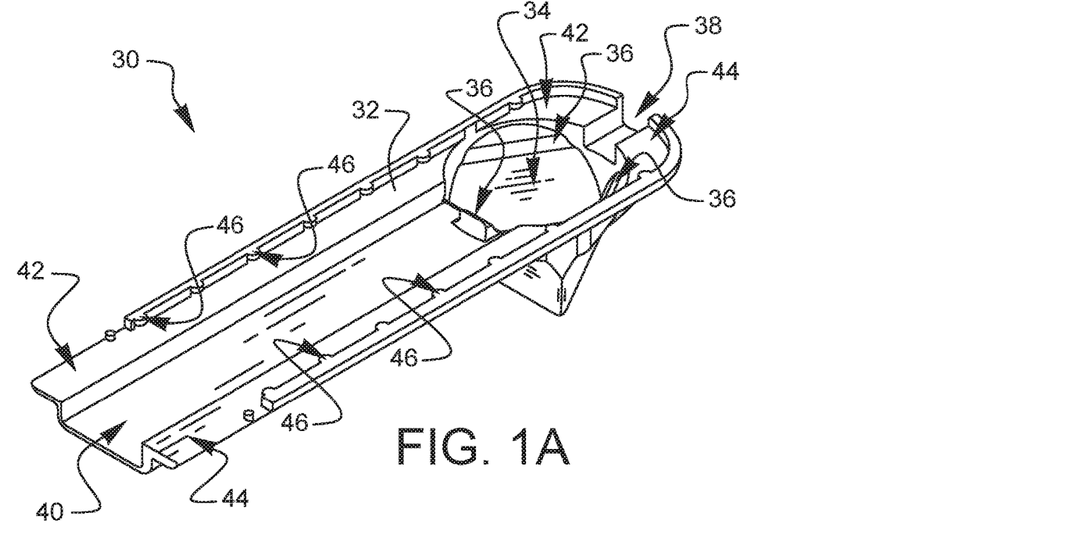
FIGS. 1A and 1B are top and bottom perspective views, respectively of one embodiment of a valve insertion tool.
Figure 1B:
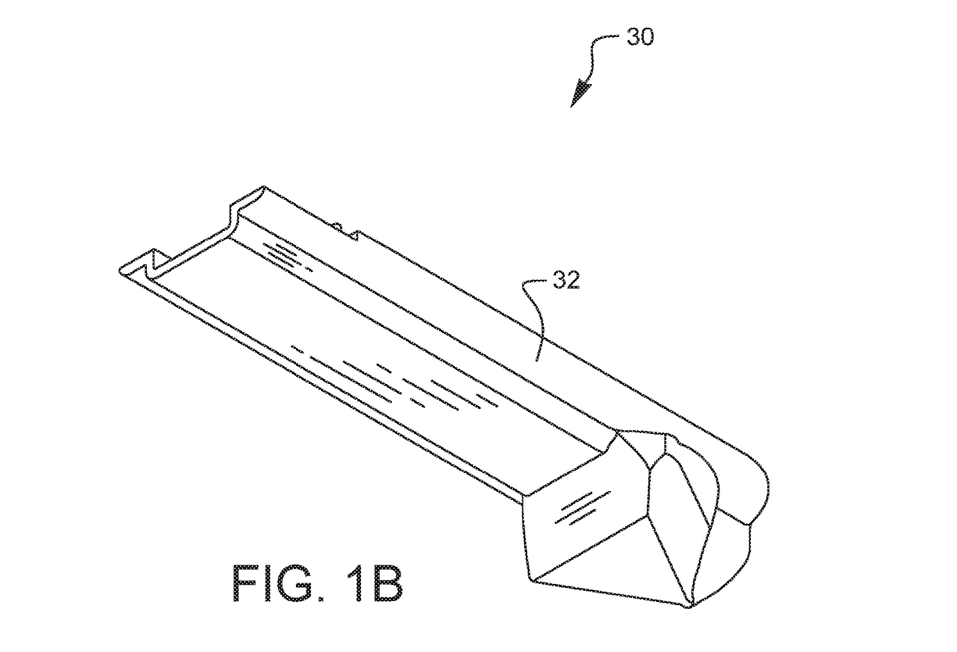

FIGS. 1A and 1B are top and bottom perspective views, respectively of one embodiment of a valve insertion tool 30. The tool 30 has a delivery housing 32 that has a prosthetic valve recess 34. On the edges of the valve recess 34, there are a plurality of cuff supports 36 configured to support a sewing cuff of a prosthetic valve (not shown in this view) while the valve's leaflets are extended down into the valve recess 34.

A distal suture channel 38 extends distally in the housing 32 from the valve recess 34. Likewise, a proximal suture channel 40 extends proximally in the housing 32 from the valve recess 34. When a prosthetic cardiac valve is ready to be inserted into a patient's thoracic cavity, the sewing cuff of the valve will already have a series of sutures stitched through it. When the valve is placed into the valve recess 34, the sutures extending into the patient can be placed into the distal suture channel 38, and the sutures extending from the valve cuff to the suture ends can be placed into the proximal suture channel 40. This embodiment of a valve insertion tool 30 has one or more shelves 42 on one side of the suture channels 38, 40 and another one or more shelves 44 on the opposite side of the suture channels 38, 40. The valve insertion tool 30 also has a series of lips 46 on either side of the delivery housing 32, extending over portions of the shelves 42, 44.

Figure 2:
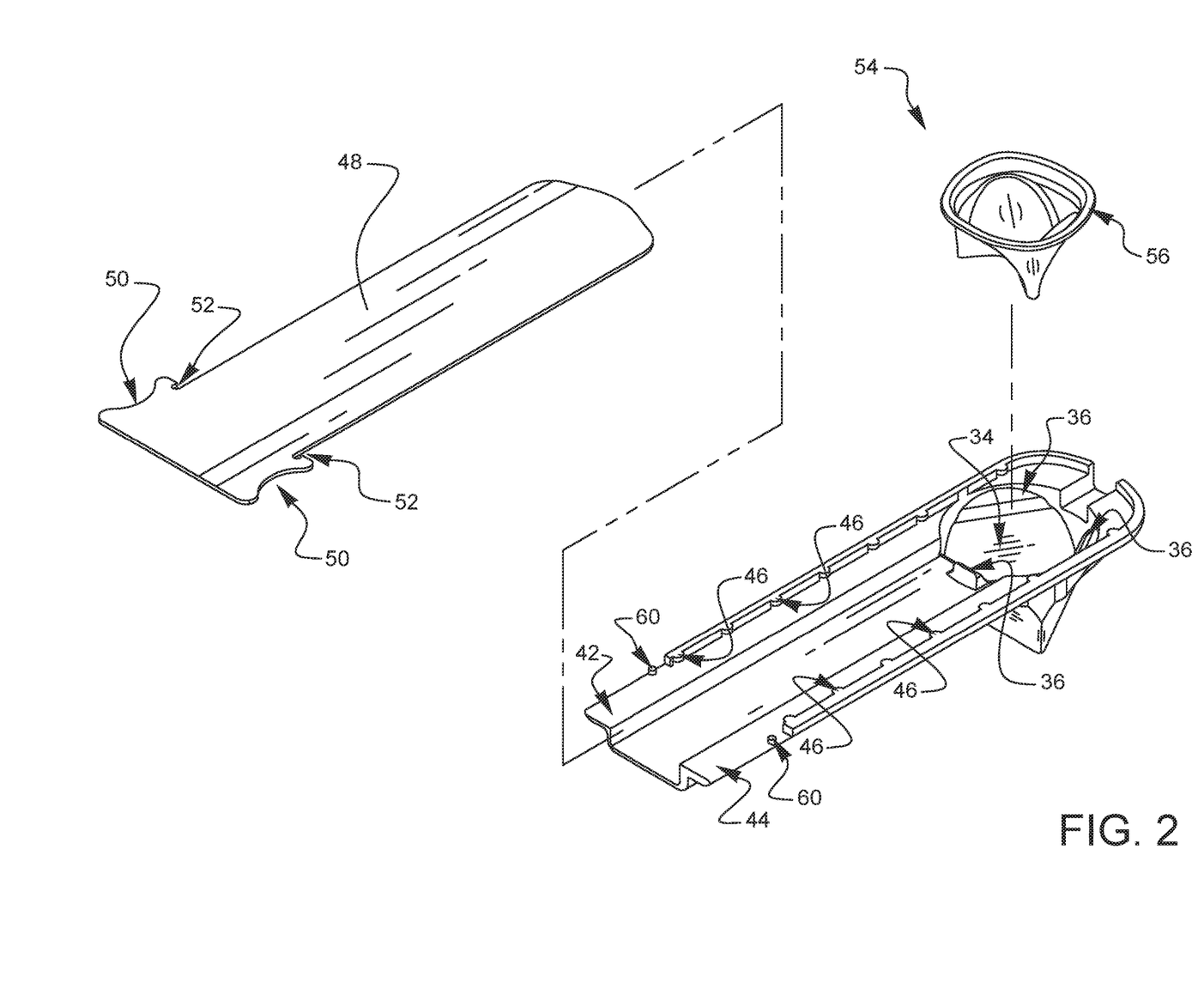
FIG. 2 is an exploded view of the valve insertion tool of FIGS. 1A and 1B.
Figure 3A:
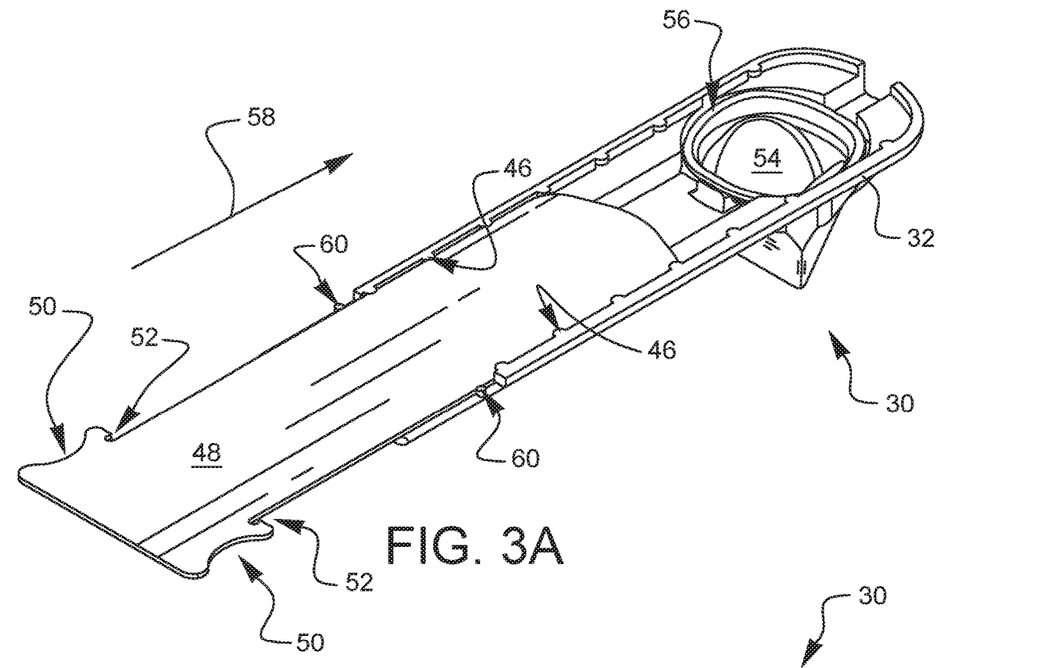
FIGS. 3A and 3B are top perspective views of the valve insertion tool of FIGS. 1A and 1B showing the installation of a cover.
Figure 3B:
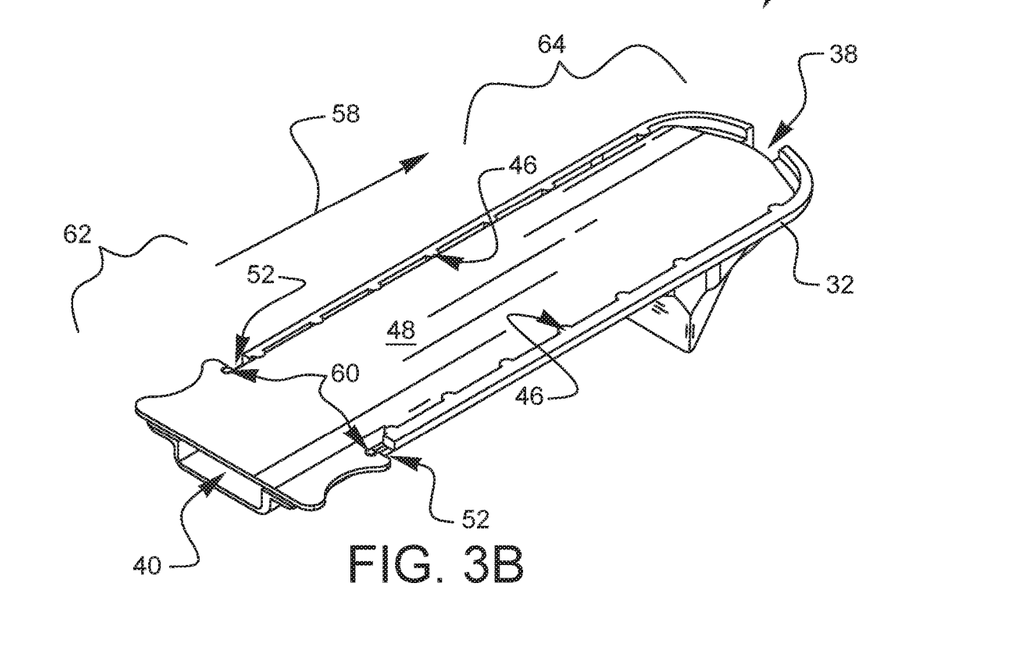

FIG. 2 shows an exploded view of the valve insertion tool 30 which includes a cover 48 having grips 50 and connection features 52. After a valve 54 having a sewing cuff 56 is lowered into the valve recess 34 so that the sewing cuff 56 rests on the cuff supports 36, the cover 48 is placed against the shelves 42, 44 and slid distally under the lips 46 as shown in FIG. 3A. The cover 48 is slid distally 58 until the connection features 52 engage tabs 60. At this point, the valve 54 is covered and protected. For simplicity, the sutures extending through the valve sewing cuff are not shown passing out of the distal suture channel 38 or the proximal suture channel 40. The proximal end 62 of the valve insertion tool 30 may then be held to manipulate the valve end 64 through an incision and into the thoracic cavity. The incision only needs to be large enough for the valve insertion tool 30 to fit through, and it is acceptable if the valve insertion tool 30 comes into contact with the tissue around the incision since the valve 54 is protected within the tool 30. Once the valve end 64 is inside the patient, the cover 48 may be removed, the valve carefully tipped out or otherwise removed from the valve recess, and the housing 32 is removed from the patient as well, leaving the valve inside the patient for further parachuting into place prior to fastening the valve into place within the heart.

Figure 4:
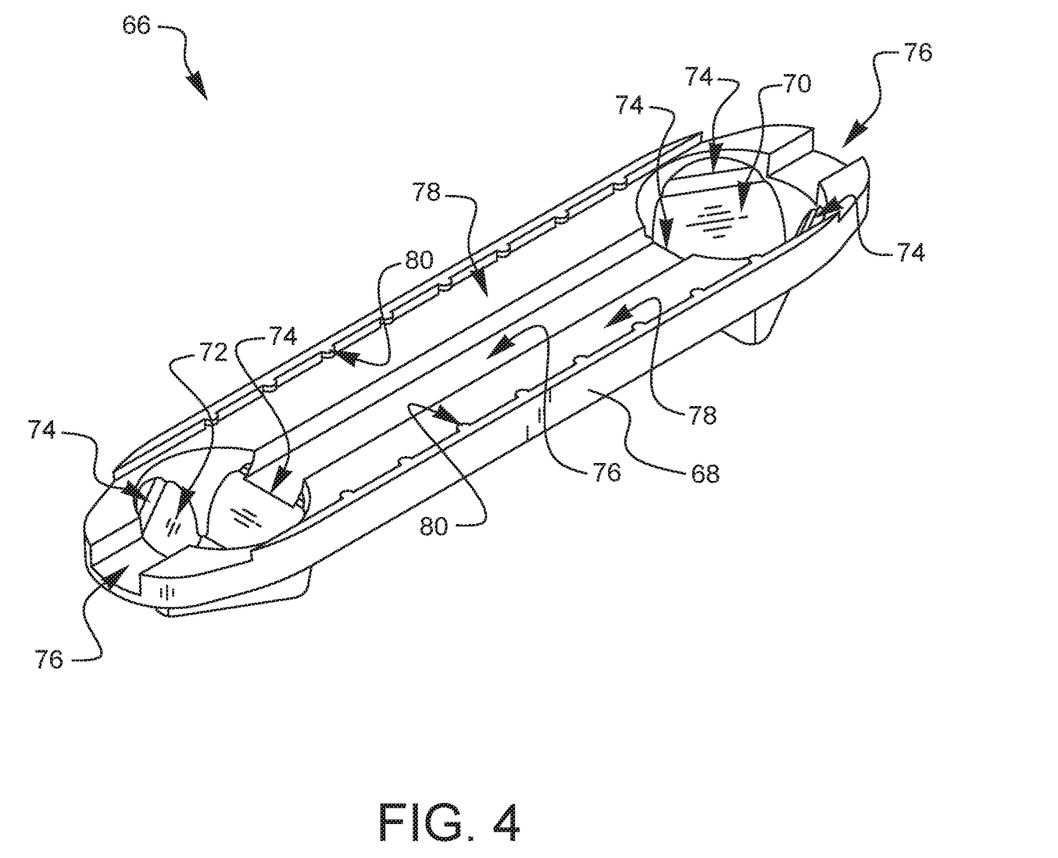
FIG. 4 is a top perspective of another embodiment of a valve insertion tool.

FIG. 4 illustrates another embodiment of a valve insertion tool 66. The valve insertion tool 66 is double ended. The tool 66 has a delivery housing 68 that has a first prosthetic valve recess 70 on one end and a second prosthetic valve recess 72 on the other end. On the edges of each of the valve recesses 70, 72, there are a plurality of cuff supports 74 configured to support a sewing cuff of a prosthetic valve (not shown in this view) while the valve's leaflets are extended down into one of the valve recesses 70, 72. The embodiment of FIG. 4 may be advantageous because prosthetic heart valves come in a wide variety of sizes or shapes, and this embodiment allows a single valve insertion tool 66 to have two different sized valve recesses 70, 72. Other embodiments may have multiple valve recesses having different shapes as well. The distal and proximal orientation of the tool 66 will depend on which valve recess 70, 72 is used for the valve. The end which holds the valve will be the distal end, and the opposite end will be the proximal end. A suture channel 76 extends down the housing from the proximal end to the distal end. When a prosthetic cardiac valve is ready to be inserted into a patient's thoracic cavity, the sewing cuff of the valve will already have a series of sutures stitched through it. When the valve is placed into the desired valve recess 70, 72, the sutures can extend in two different directions (distally and proximally) within the suture channel 76. This embodiment of a valve insertion tool 66 has one or more shelves 78 both sides of the suture channel 76. The valve insertion tool 66 also has a series of lips 80 on either side of the delivery housing 68, extending over portions of the shelves 78. A cover (not shown in this view) can be slid along the shelves 78 and under the lips 80 from either end of the tool 66 to hold a valve in place within the tool 66 until the valve has been inserted into the thoracic cavity.

Figure 5:
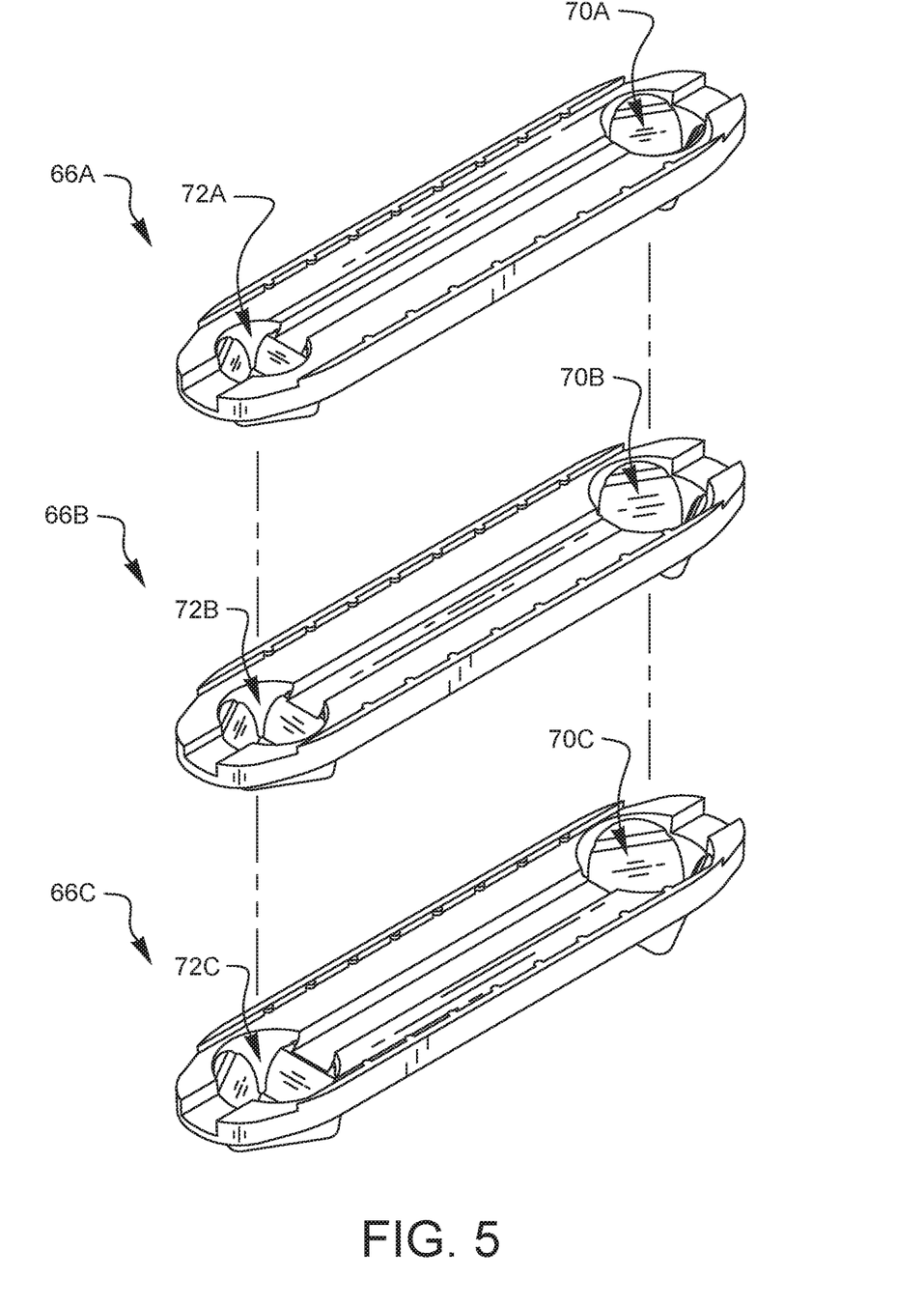
FIG. 5 is an exploded view of an assembly of multiple valve insertion tools similar to the embodiment shown in FIG. 4.
Figure 6:
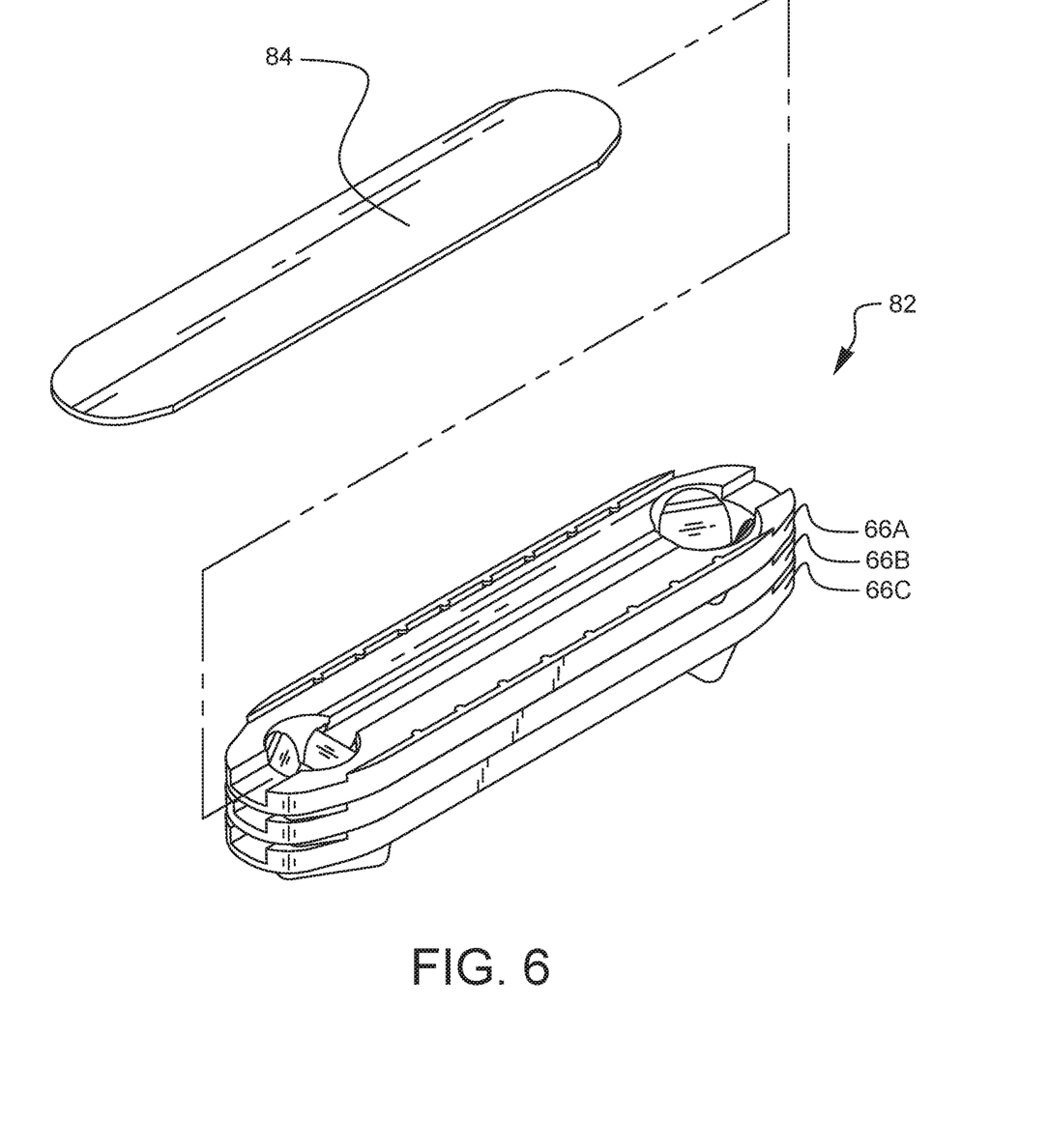
FIG. 6 is a top perspective view of the valve insertion tool assembly of FIG. 5 showing the installation of a cover.

FIG. 5 is an exploded view of an assembly of multiple valve insertion tools 66A, 66B, and 66C, each one similar to the tool 66 discussed above, but each having different sized valve recess 70A, 72A, 70B, 72B, 70C, and 72C. Recess 72C is larger than recess 72B, which is larger than recess 72A. Likewise, recess 70C is larger than recess 70B, which is larger than recess 70A. This enables the set of tools 66A, 66B, and 66C to be stacked or stackable in a kit 82 shown in FIG. 6. A single cover 84 may be included with the kit 82 and utilized as described above with the tool 66A, 66B, 66C which is chosen as the needed size during a surgical procedure.

Figure 7A:
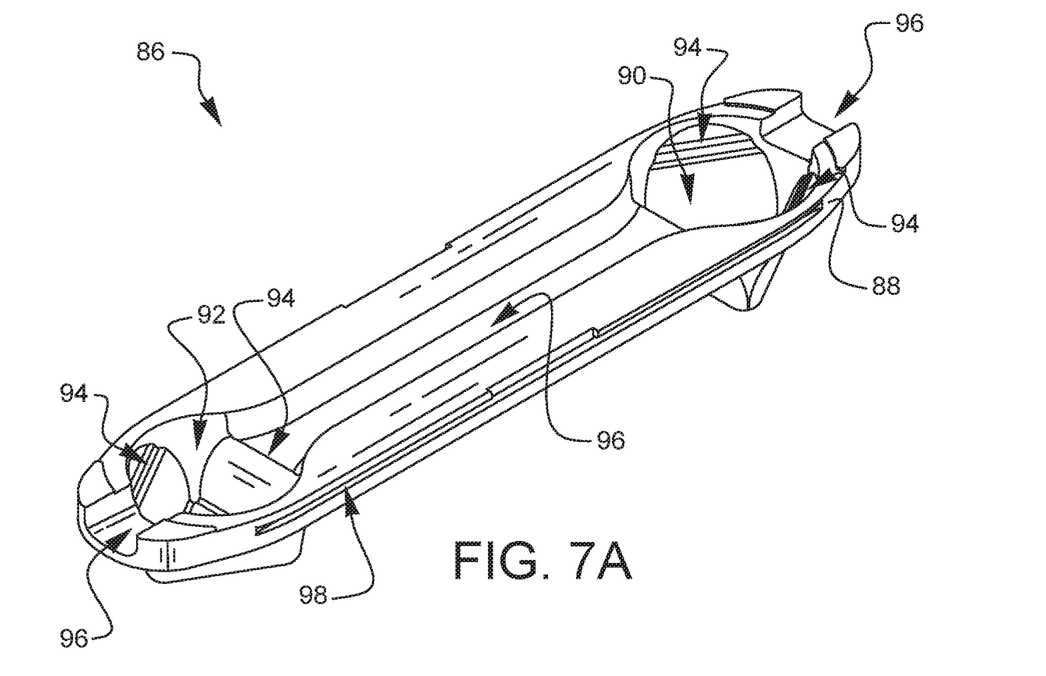
FIGS. 7A and 7B are top and bottom perspective views, respectively, of another embodiment of a valve insertion tool.
Figure 7B:
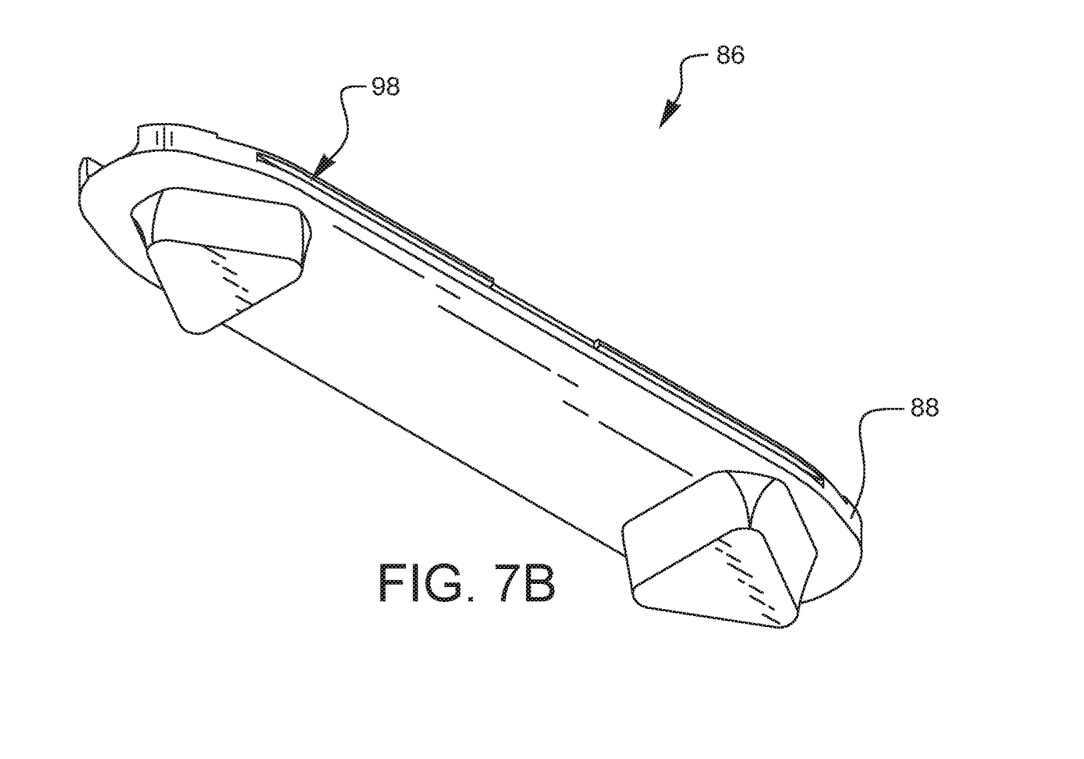

FIGS. 7A and 7B are top and bottom perspective views, respectively of another embodiment of a valve insertion tool 86. The tool 86 has a delivery housing 88 that has a first prosthetic valve recess 90 on one end and a second prosthetic valve recess 92 on the other end. On the edges of each of the valve recesses 90, 92, there are a plurality of cuff supports 94 configured to support a sewing cuff of a prosthetic valve (not shown in this view) while the valve's leaflets are extended down into one of the valve recesses 90, 92. This embodiment may be advantageous because prosthetic heart valves come in a wide variety of sizes, and this embodiment allows a single valve insertion tool 86 to have two different sized valve recesses 90, 92. The distal and proximal orientation of the tool 86 will depend on which valve recess 90, 92 is used for the valve. The end which holds the valve will be the distal end, and the opposite end will be the proximal end. A suture channel 96 extends down the housing from the proximal end to the distal end. When a prosthetic cardiac valve is ready to be inserted into a patient's thoracic cavity, the sewing cuff of the valve will already have a series of sutures stitched through it. When the valve is placed into the desired valve recess 90, 92, the sutures can extend in two different directions (distally and proximally) within the suture channel 96. This embodiment of a valve insertion tool 86 has grooves 98 on either side of the outside of the housing 88 (the grooves 98 are only visible on one side of the housing 88 in the views of FIGS. 7A, 7B, but the grooves 98 on the opposite side are symmetrically located). A cover (not shown in this view) can be slid over the top of the housing 88 and around the sides of the housing 88 and into engagement with the grooves 98 in order to hold the cover in place while to valve is being delivered with the tool 86.

Figure 8:
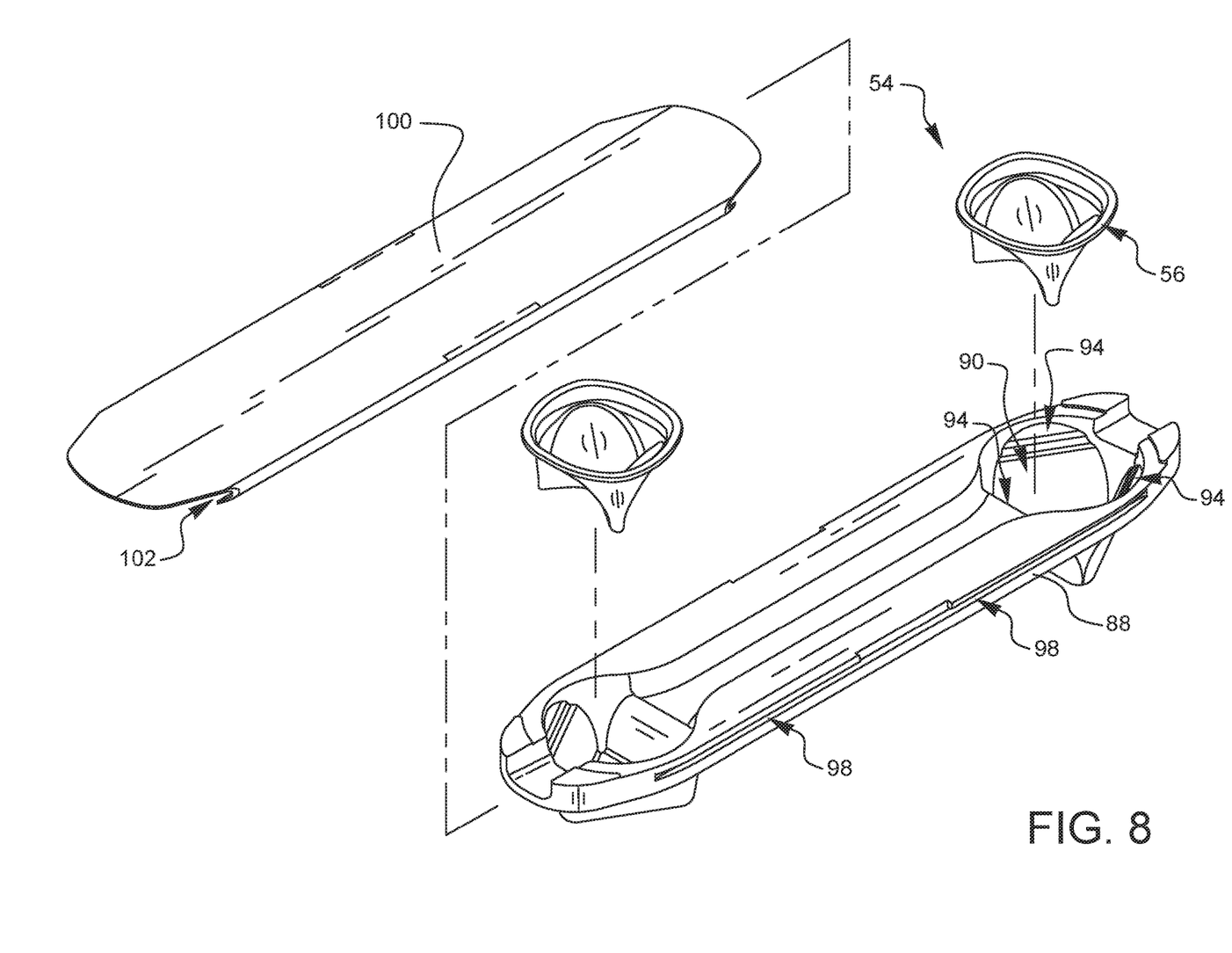
FIG. 8 is an exploded view of an assembly of the valve insertion tool of FIGS. 7A and 7B.

FIG. 8 shows an exploded view of the valve insertion tool 86 which includes a cover 100 having rolled edges 102 (only visible on one side, but there are symmetrical rolled edges on the opposite facing side). After a valve 54 having a sewing cuff 56 is lowered into the desired valve recess 90 so that the sewing cuff 56 rests on the cuff supports 94, the cover 100 is placed over the top of the housing 88 so that the rolled edges 102 either slide into or snap into the grooves 98 in the housing.

Figure 9A:
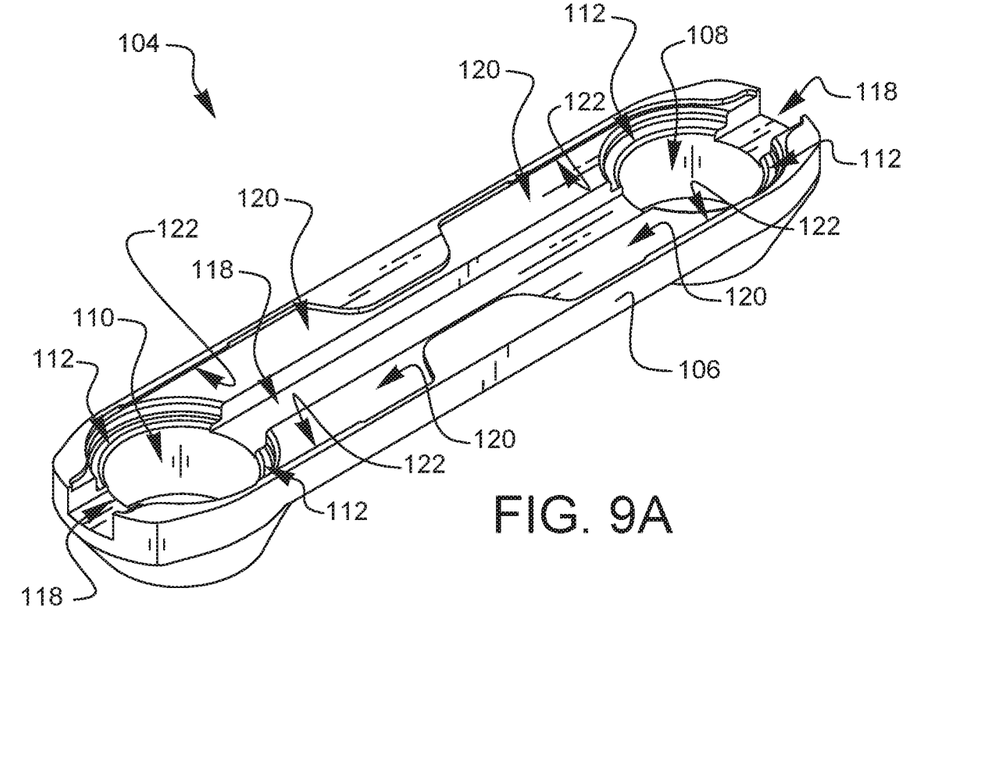
FIGS. 9A and 9B are top and bottom perspective views, respectively, of another embodiment of a valve insertion tool.
Figure 9B:
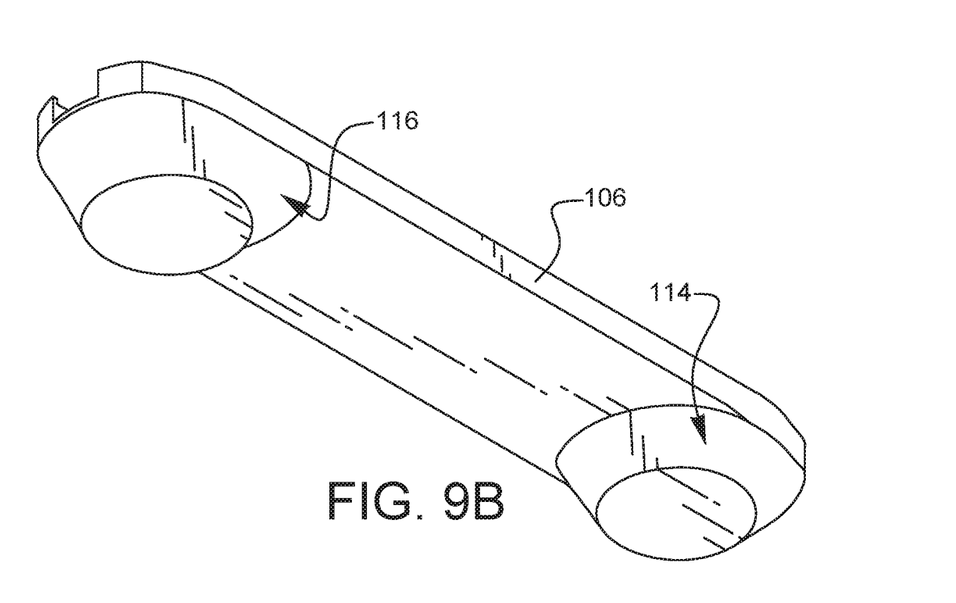

FIGS. 9A and 9B are top and bottom perspective views, respectively of another embodiment of a valve insertion tool 104. The tool 104 has a delivery housing 106 that has a first prosthetic valve recess 108 on one end and a second prosthetic valve recess 110 on the other end. On the edges of each of the valve recesses 108, 110, there are a plurality of cuff supports 112 configured to support a sewing cuff of a prosthetic valve (not shown in this view) while the valve's leaflets are extended down into one of the valve recesses 108, 110. This embodiment may be advantageous because prosthetic heart valves come in a wide variety of sizes, and this embodiment allows a single valve insertion tool 104 to have two different sized valve recesses 108, 110. Looking at the bottom view of FIG. 9B, this embodiment also has the feature that the housing 106 on the outsides walls 114, 116 of the valve recesses 108, 110 is smoothed to avoid the sharper contours of the previous embodiments, resulting in atraumatic outer housing walls. This can be advantageous when inserting the tool 104 through an incision as it may be less traumatic, causing minimal tissue injury during use. The distal and proximal orientation of the tool 104 will depend on which valve recess 108, 110 is used for the valve. The end which holds the valve will be the distal end, and the opposite end will be the proximal end. A suture channel 118 extends down the housing 106 from the proximal end to the distal end. When a prosthetic cardiac valve is ready to be inserted into a patient's thoracic cavity, the sewing cuff of the valve will already have a series of sutures stitched through it. When the valve is placed into the desired valve recess 108, 110, the sutures can extend in two different directions (distally and proximally) within the suture channel 118. This embodiment of a valve insertion tool 104 has a recessed shelf 120 on both ends of the housing 106. A portion of the shelves 120 has a lip 122 which can be used to hold a cover (not shown in this view) over the valve recess 108, 110 being used.

Figure 10A:
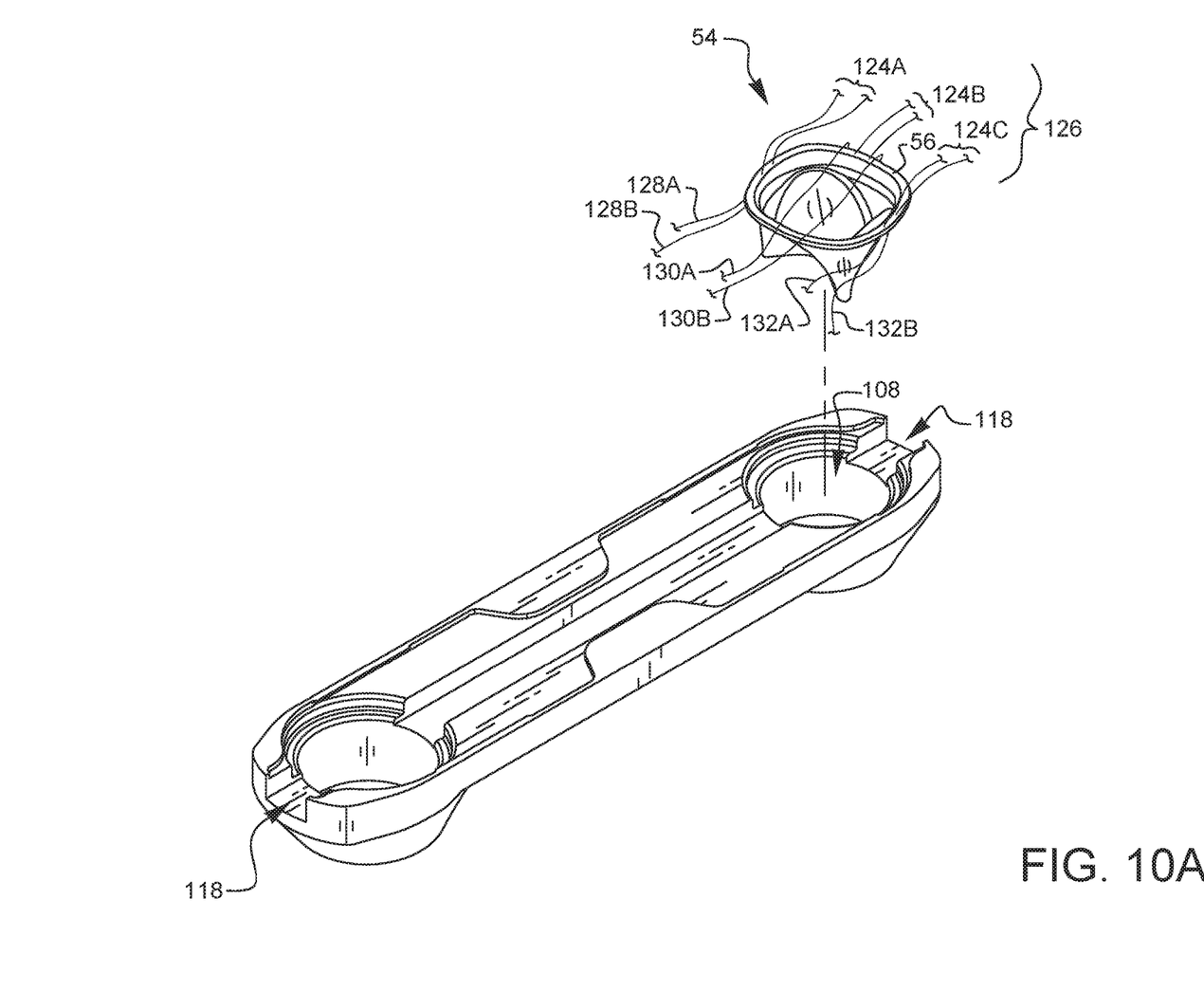
FIGS. 10A-10D are perspective views of the assembly of a valve insertion kit, illustrating the loading of a pre-sutured valve into another embodiment of a valve insertion tool.
Figure 10B:
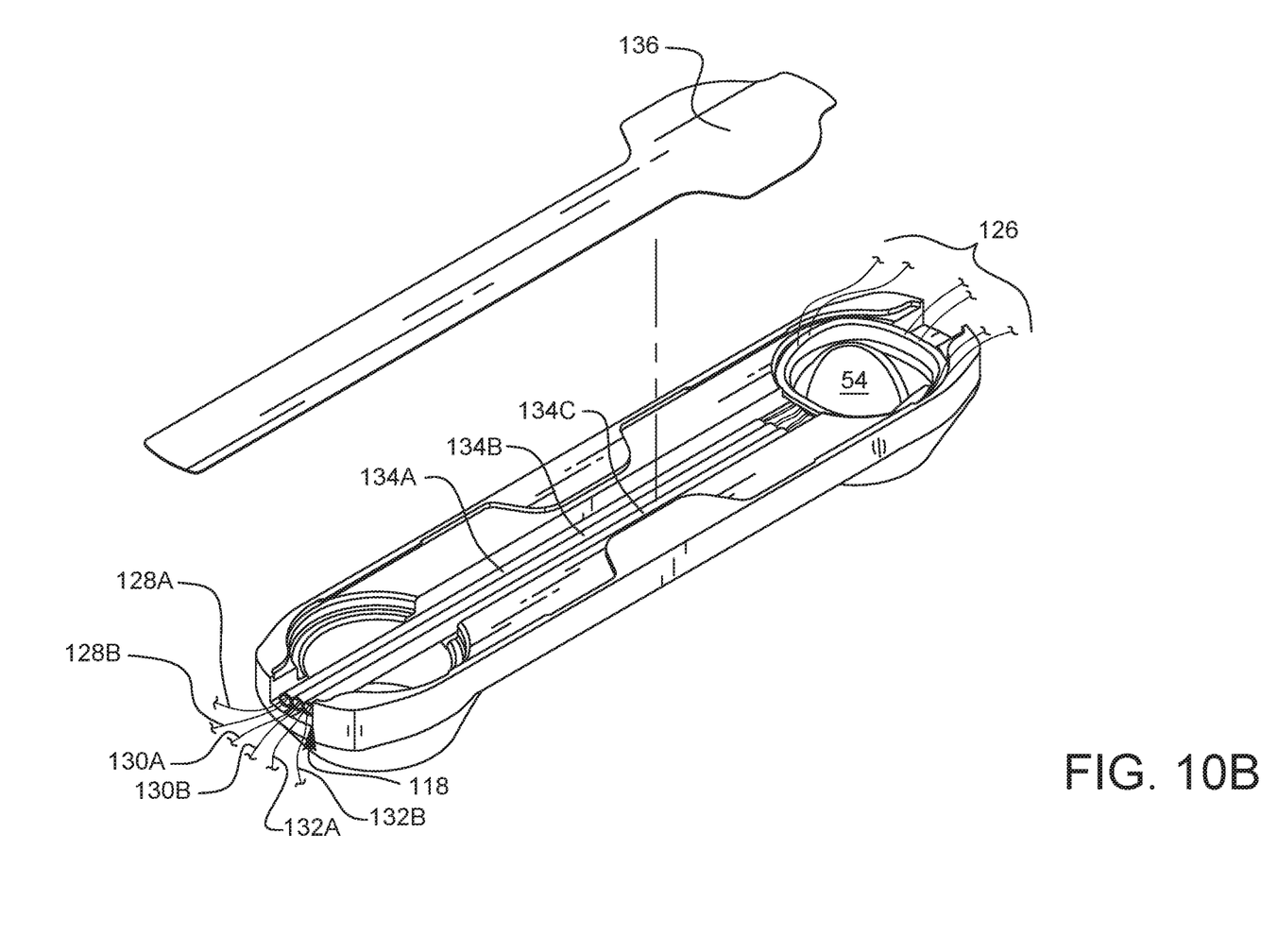
Figure 10C:
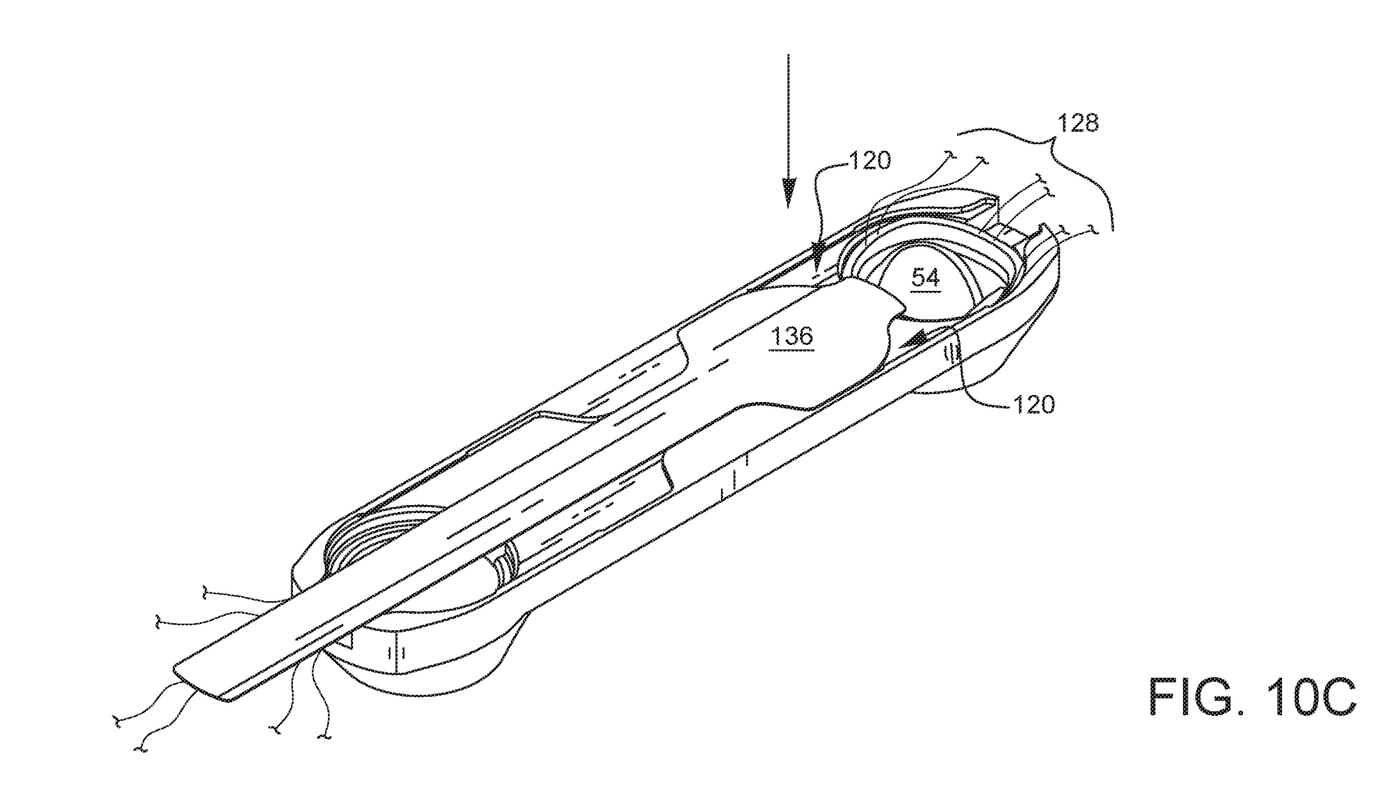
Figure 10D:
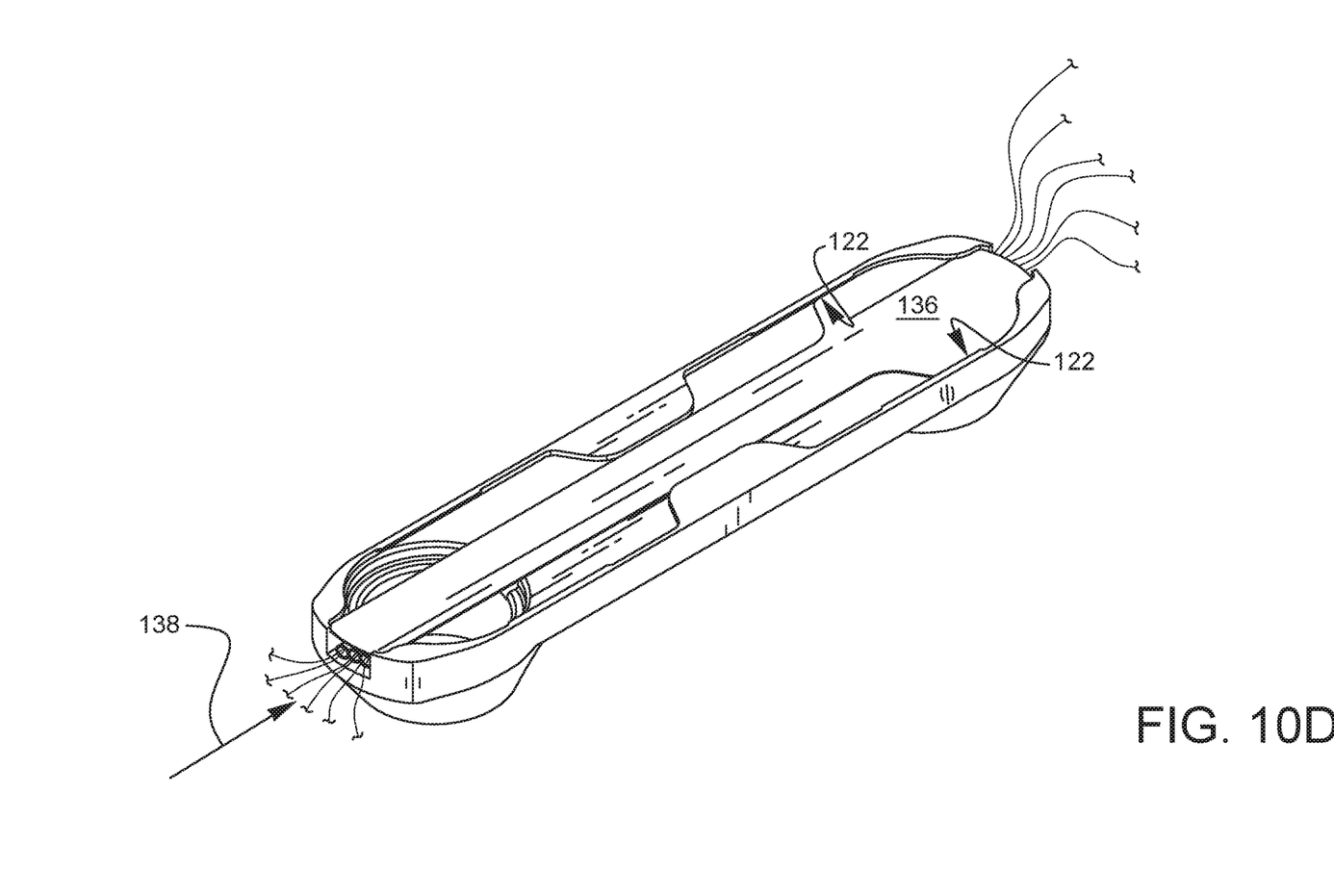

FIG. 10A illustrates a valve 54 which has three sutures 124A, 124B, and 124C stitched through its sewing cuff 56. Although each suture 124A, 124B, 124C may at first look like two separate sutures, it should be understood that the distal end 126 of each suture 124A, 124B, 124C is a loop which is sutured through an aortic annulus (not shown), so what are seen are ends 128A, 128B of suture 124A which have been passed through the sewing cuff 56 of the aortic valve 54. Likewise, ends 130A, 130B of suture 124B have been passed through the sewing cuff 56. Similarly, ends 132A, 132B of suture 124C have been passed through the sewing cuff 56. The sutures 124A, 124B, 124C and their ends 128A, 128B, 130A, 130B, 132A, 132B can be placed into the suture channel 118 when the valve 54 is placed into the desired valve recess 108. Alternately, each pair of suture ends 128A/128B, 130A/130B, and 132A/132B may be snared through a corresponding semi-rigid or rigid tube 134A, 134B, 134C as shown in FIG. 10B. The tubes 134A, 134B, 134C may be placed into the suture channels 118 and then the cover 136 brought into alignment as shown in FIG. 10B. The cover 136 can be set down on the appropriate shelf 120 as shown in FIG. 10C and then slid distally 138 underneath the lips 122 to hold the valve in place for insertion in the thoracic cavity as with the above embodiments.

Once the valve is inside the thoracic cavity and the valve insertion tool 104 and its cover 136 have been removed, the suture ends extending proximally from each tube may be cinched while holding each tube to hold the distal end of the tube against the sewing cuff of the valve. The tubes can then be manipulated to help move the valve within the thoracic cavity. When the valve is properly positioned, the tubes can be removed and the suture ends fastened against the sewing cuff to hold the valve in place.

In actual practice, there will usually be far more than three sets of suture ends stitched through a prosthetic valve. If using the tube method with the valve insertion tool, it is not necessary to place each set of suture ends through a tube. Using three tubes, one for each of the three commissure stitches in the valve sewing cuff, may be sufficient to manipulate the valve while the valve is parachuted down the remainder of the sutures in a more traditional fashion.

Various advantages of a valve insertion tool have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A valve insertion tool, comprising:
   a housing;
   at least one valve recess defined by the housing, wherein the housing defines a first valve recess and a second valve recess;
   a suture channel passing from a distal end of the housing to a proximal end of the housing; and
   a cover configured to engage the housing for covering the at least one valve recess and a top of the suture channel.

2. The valve insertion tool of claim 1, wherein the first valve recess is a different shape than the second valve recess.

3. The valve insertion tool of claim 1, wherein the first valve recess is a different size than the second valve recess.

4. The valve insertion tool of claim 1, wherein the first valve recess is the same shape and same size as the second valve recess.

5. The valve insertion tool of claim 1, wherein the first valve recess and the second valve recess have atraumatic outer housing walls.

6. The valve insertion tool of claim 1, wherein the at least one valve recess is configured to be stacked with one or more additional valve insertion tools.

7. The valve insertion tool of claim 1, wherein the housing defines one or more grooves configured to engage the cover.

8. The valve insertion tool of claim 7, the cover further comprising rolled edges configured to engage one or more grooves on the housing.

9. The valve insertion tool of claim 1, wherein the housing defines one or more lips configured to engage the cover.

10. A valve insertion kit, comprising:
    at least one valve insertion tool comprising a housing and a suture channel, wherein:
    the housing defines at least one valve recess; and
    the suture channel passes from a distal end of the housing to a proximal end of the housing;
    at least one valve having at least one suture stitched into a sewing cuff on the valve, at least a portion of the at least one suture located within the suture channel; and
    a cover configured to engage the housing for covering the at least one valve recess and a top of the suture channel.

11. The valve insertion kit of claim 10, wherein the housing of the at least one valve insertion tool is configured to be stackable with a housing of a second valve insertion tool.

12. A valve insertion tool, comprising:
    a housing having a distal end and a proximal end;
    at least one valve recess defined by the housing;
    a suture channel passing from a first port at the distal end of the housing to a second port at the proximal end of the housing; and
    a cover configured to engage the housing for (i) covering the at least one valve recess and a top of the suture channel, and (ii) maintaining an external access to at least one of the first port and the second port.

13. The valve insertion tool of claim 12, further comprising a valve retained within the at least one valve recess.

14. The valve insertion tool of claim 13, wherein the valve includes a sewing cuff.

* * * * *